(12) United States Patent
Soundarrajan et al.

(10) Patent No.: US 10,401,340 B2
(45) Date of Patent: Sep. 3, 2019

(54) MEASUREMENT OF HAZARDOUS GASES IN HYDRAULIC FRACKING SITES

(71) Applicant: Honeywell International Inc., Morristown, NJ (US)

(72) Inventors: Prabhu Soundarrajan, Valencia, CA (US); Viktor Konovalov, Corona, CA (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 603 days.

(21) Appl. No.: 14/576,311

(22) Filed: Dec. 19, 2014

(65) Prior Publication Data

US 2015/0219609 A1 Aug. 6, 2015

Related U.S. Application Data

(60) Provisional application No. 61/934,065, filed on Jan. 31, 2014.

(51) Int. Cl.

| | |
|---|---|
| G01D 18/00 | (2006.01) |
| G01N 33/00 | (2006.01) |
| G01N 21/00 | (2006.01) |
| G01N 33/22 | (2006.01) |
| E21B 49/08 | (2006.01) |
| G01M 3/22 | (2006.01) |
| G01P 21/00 | (2006.01) |
| G01N 21/27 | (2006.01) |

(52) U.S. Cl.
CPC ....... *G01N 33/0006* (2013.01); *E21B 49/087* (2013.01); *G01M 3/22* (2013.01); *G01N 33/0036* (2013.01); *G01N 33/0057* (2013.01); *G01N 33/225* (2013.01); *G01D 18/00* (2013.01); *G01N 21/274* (2013.01); *G01N 2201/12746* (2013.01); *G01P 21/00* (2013.01)

(58) Field of Classification Search
CPC .......... G01N 33/0006; G01N 33/0036; G01N 33/0057; G01N 33/225; E21B 49/087; G01M 3/22
USPC ........................................................ 702/104
See application file for complete search history.

(56) References Cited

U.S. PATENT DOCUMENTS

| | | | | |
|---|---|---|---|---|
| 3,690,167 A | * | 9/1972 | Chase, Jr. ............... | E21B 49/00 250/260 |
| 3,702,397 A | * | 11/1972 | Firth ....................... | G01J 3/108 250/338.1 |
| 3,819,276 A | * | 6/1974 | Kiess ..................... | G01N 21/27 250/564 |
| 3,864,628 A | * | 2/1975 | Klass ................. | G01N 33/0014 324/71.1 |

(Continued)

OTHER PUBLICATIONS

EPA Method TO-15 from the Compendium of Methods for the Determination of Toxic Organic Compounds in Ambient Air, Second Edition (EPA/625/R-96/010b), Jan. 1999.

(Continued)

*Primary Examiner* — Ly D Pham
(74) *Attorney, Agent, or Firm* — Wick Phillips Gould & Martin, LLP

(57) ABSTRACT

This application discloses a method and an apparatus for the measurement of gases in hydraulic fracking sites, comprising a gas sensor, a computer, and a correction factor wherein the correction factor is applied to the observed gas reading to generate a more accurate reading of the gas level at the site.

17 Claims, 9 Drawing Sheets

(56) References Cited

U.S. PATENT DOCUMENTS

| | | | | |
|---|---|---|---|---|
| 4,063,898 | A * | 12/1977 | Fisher | G01N 25/32 136/225 |
| 4,635,735 | A * | 1/1987 | Crownover | E21B 21/067 175/42 |
| 4,810,876 | A * | 3/1989 | Wraight | G01V 5/10 250/256 |
| 5,221,445 | A * | 6/1993 | Wang | G01N 27/4065 204/425 |
| 6,229,308 | B1 * | 5/2001 | Freedman | G01N 24/081 324/300 |
| 8,852,513 | B1 * | 10/2014 | Speer | G01N 33/0014 204/424 |
| 2003/0200796 | A1 * | 10/2003 | Pawliszyn | G01N 30/00 73/64.47 |
| 2005/0170226 | A1 * | 8/2005 | Kralick | H01M 8/04223 73/23.2 |
| 2005/0217479 | A1 * | 10/2005 | Hale | B01D 53/228 95/53 |
| 2007/0050154 | A1 * | 3/2007 | Albahri | G01N 25/14 702/22 |
| 2008/0119753 | A1 * | 5/2008 | Ricciardelli | A61B 5/097 600/532 |
| 2008/0146761 | A1 * | 6/2008 | Kawashima | C08F 210/16 526/348.5 |
| 2010/0204925 | A1 * | 8/2010 | Albahri | G01N 25/14 702/25 |
| 2010/0212893 | A1 * | 8/2010 | Moini Araghi | E21B 43/24 166/272.1 |
| 2012/0042777 | A1 * | 2/2012 | Lee | B01D 53/228 95/47 |
| 2012/0312497 | A1 * | 12/2012 | Parida | F28D 7/085 165/11.1 |
| 2012/0329958 | A1 * | 12/2012 | Freeman | C08J 5/18 525/425 |
| 2014/0208840 | A1 * | 7/2014 | Bright | G01N 33/0006 73/152.19 |
| 2016/0242682 | A1 * | 8/2016 | Gulati | A61B 5/1455 |
| 2016/0249836 | A1 * | 9/2016 | Gulati | A61B 5/1455 600/316 |
| 2017/0261207 | A1 * | 9/2017 | Knapp | F02C 7/224 |

OTHER PUBLICATIONS

Thoma et al., Facility Fence-Line Monitoring Using Passive Samplers, ISSN: 1047-3289 J. Air & Waste Manage. Assoc. 61:834-842, Aug. 2011.

Thoma et al., Assessment of Methane and VOC Emissions from Select Upstream Oil and Gas Production Operations Using Remote Measurements, Interim Report on Recent Survey.

Studies, Proceedings of 105th Annual Conference of the Air & Waste Management Association—Jun. 19-22, 2012, in San Antonio, Texas.

Graham's Law, See http://en.wikipedia.org/wiki/Graham%27s_law, Mar. 31, 2015.

* cited by examiner

MEASUREMENT OF HAZARDOUS GASES IN HYDRAULIC FRACKING SITES

CROSS REFERENCE TO RELATED APPLICATION

The present application claims priority to U.S. Provisional Application No. 61/934,065, filed Jan. 31, 2014, entitled "Measurement of Hazardous Gases in Hydraulic Fracking Sites," which is incorporated herein by reference.

FIELD OF THE INVENTION

This invention relates to an apparatus for the measurement of gases in hydraulic fracking sites and a method of measuring gases in hydraulic fracking sites.

BACKGROUND

Hydraulic fracking is creating huge energy growth around the world. Similar to the refinery and petrochemical industry, the fracking industry has concerns about combustible and toxic gases released during the production and processing of natural gas and oil from hydraulic fracking wells.

Since the hydraulic fracking is a relatively new production process, there are few rules or regulations governing the monitoring and control of the hazardous gases in the area surrounding the oil and gas production facility.

Recent reports from the Environmental Protection Agency (EPA) present a significant effort to reduce emissions from hydraulically fractured natural gas wells. The Leak Detection and Repair (LDAR) for valves are applied at 500 ppm for hydraulically fractured wells compared to 2000 ppm for refining and petrochemical processes. A key component of the rules is expected to yield a nearly 95 percent reduction in volatile organic compounds (VOCs) emitted from more than 11,000 new hydraulically fractured gas wells each year. This significant reduction would be accomplished primarily through the use of a proven process known as a "reduced emissions completion" or "green completion" to capture natural gas that currently escapes to the air.

In a green completion process, special equipment separates gas and liquid hydrocarbons from the flow back that comes from the well as it is being prepared for production. The gas and hydrocarbons can then be treated and used or sold, avoiding the waste of nonrenewable natural resources.

An estimated 11,400 new wells are fractured each year. The EPA estimates another 1,400 existing wells are re-fractured to stimulate production or to produce natural gas from a different production zone. In 2009, about 1.1 million wells were producing oil and natural gas in the United States.

Known measurement and detection techniques are directed to passive sampling of the environment around hydraulic fracking sites then calculating VOC and hazardous gas levels. These techniques are time consuming and labor intensive and are often unable to catch harmful VOC's in real-time to protect worker in hydraulic fracking sites.

In fracking sites, the gas composition is a combination of hydrocarbons. A new method and apparatus, as described herein, has been developed to accurately measure the explosive and hazardous gases in hydraulic fracking sites to ensure plant safety, personnel safety, and improved productivity.

DETAILED DESCRIPTION

Figure 1:
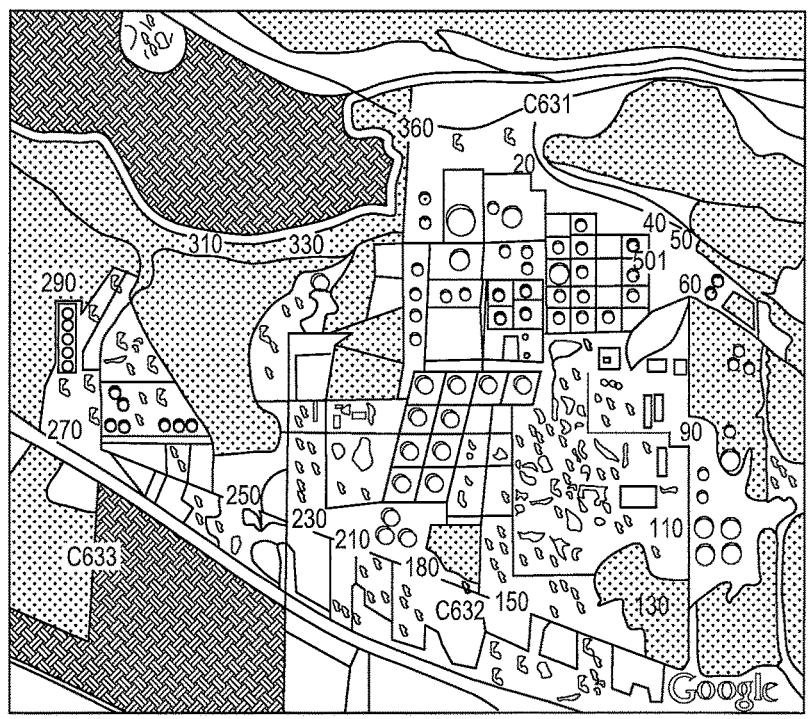
FIG. 1 illustrates prior art passive sampling for fence line monitoring across a hydraulic fracking site.
Figure 1:
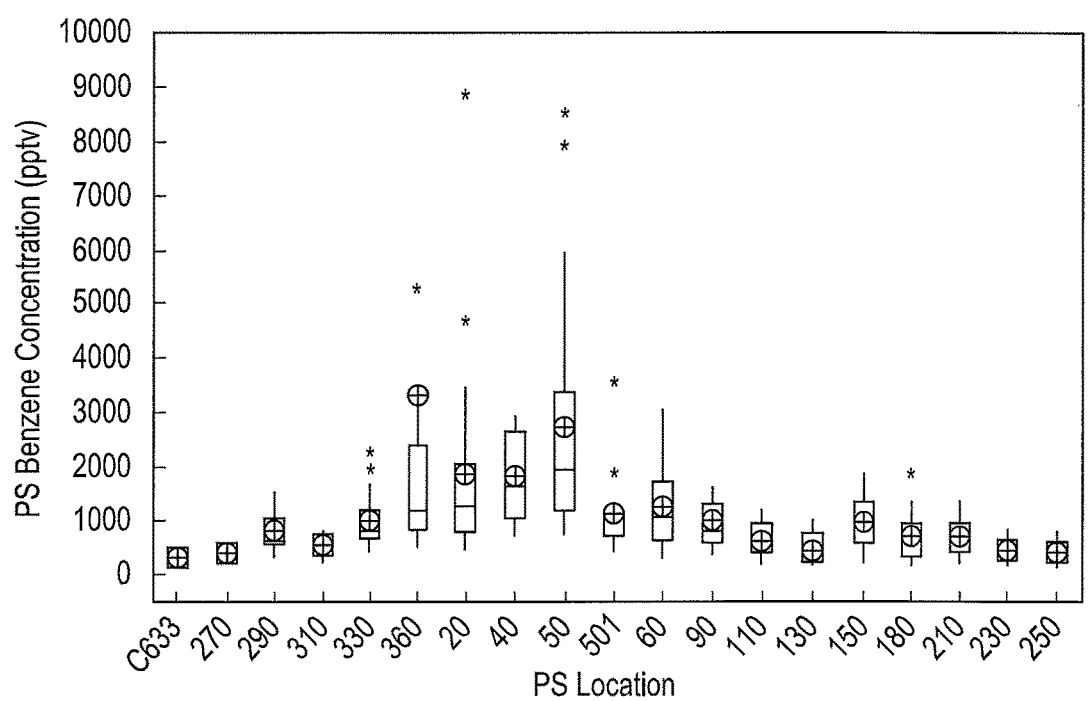
Figure 2:
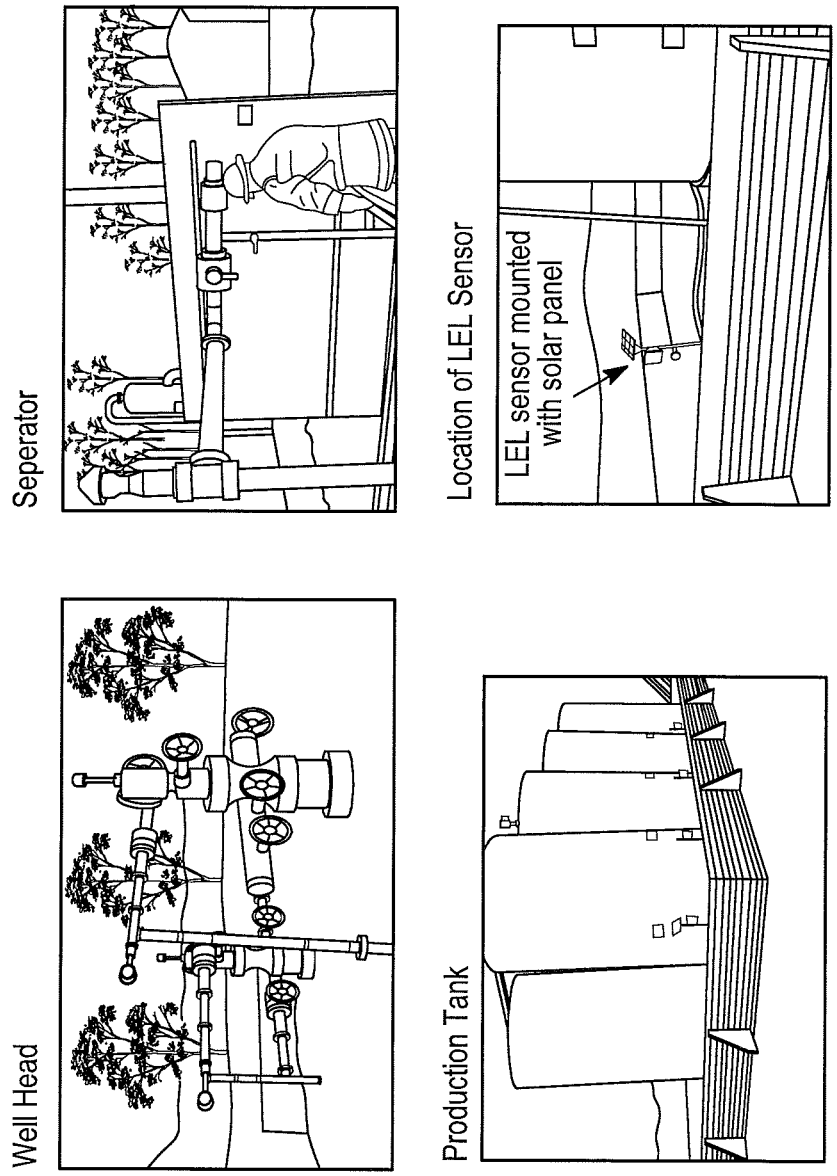
FIG. 2 illustrates sources of gas evolution in a hydraulic fracking site.
Figure 3:
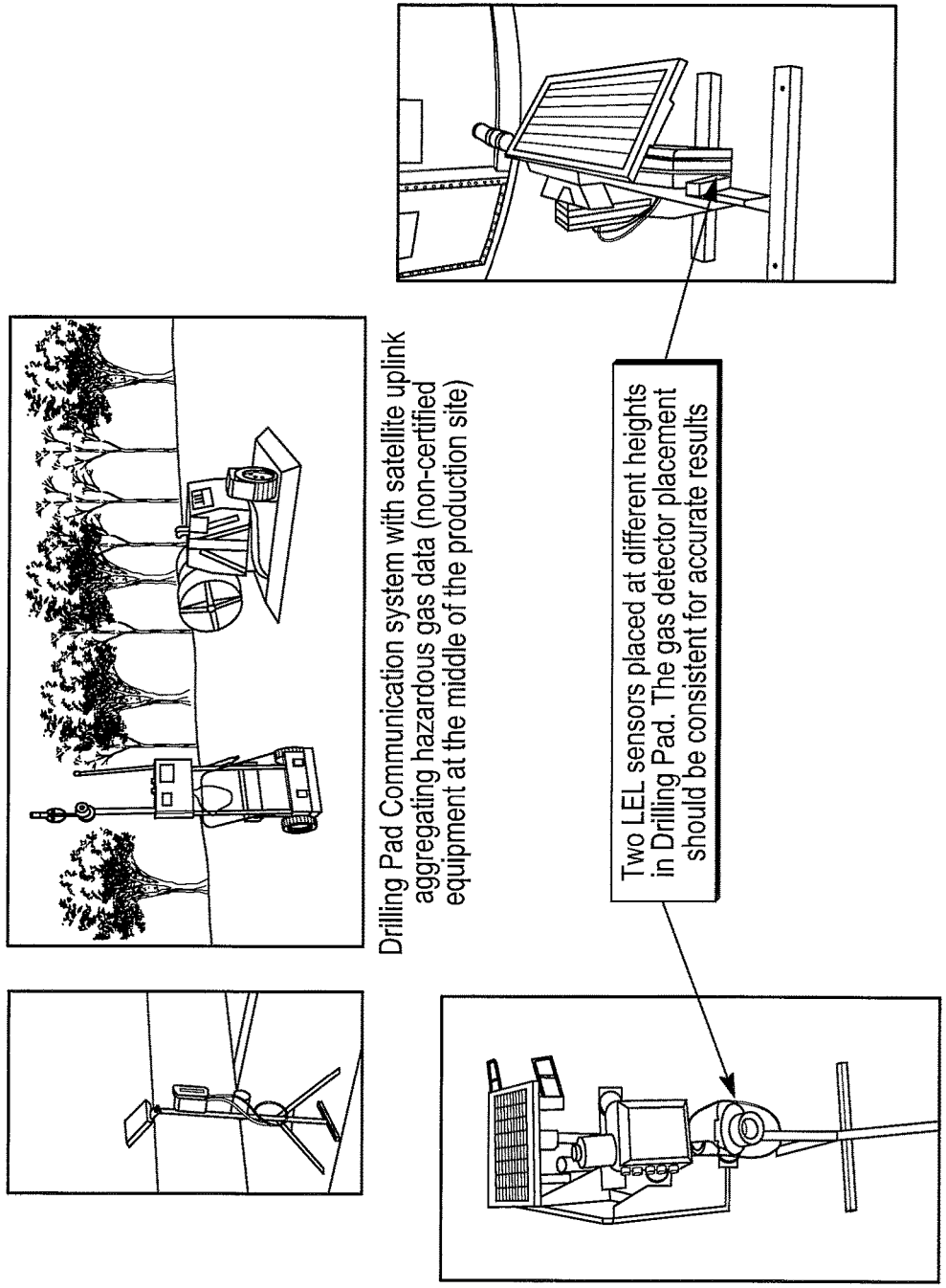
FIG. 3 illustrates the design of a gas detection system in specific location around a hydraulic fracking site.
Figure 4:
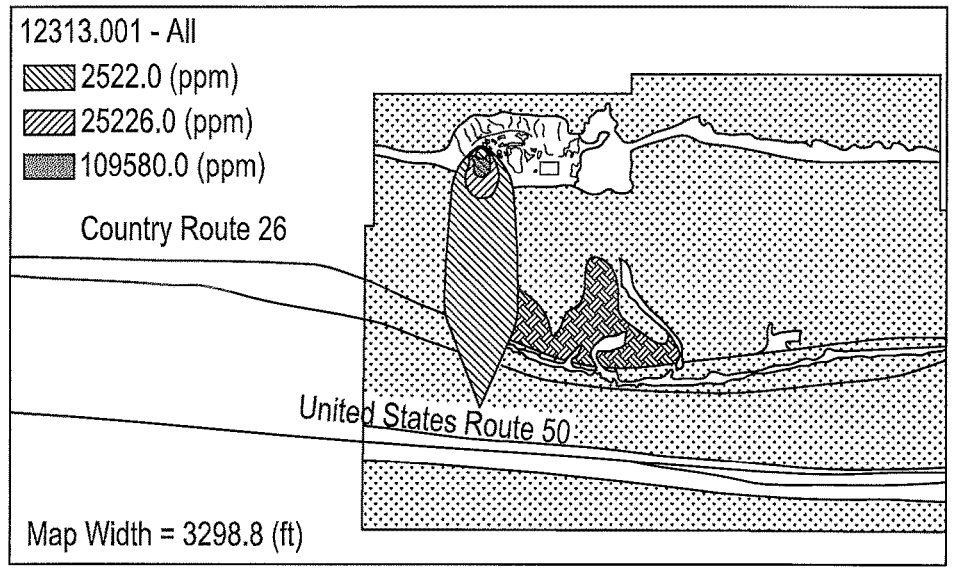
FIG. 4 illustrates the evolution of gases in hydraulic fracking site that are dependent on gas density and meteorological parameters.
Figure 4:
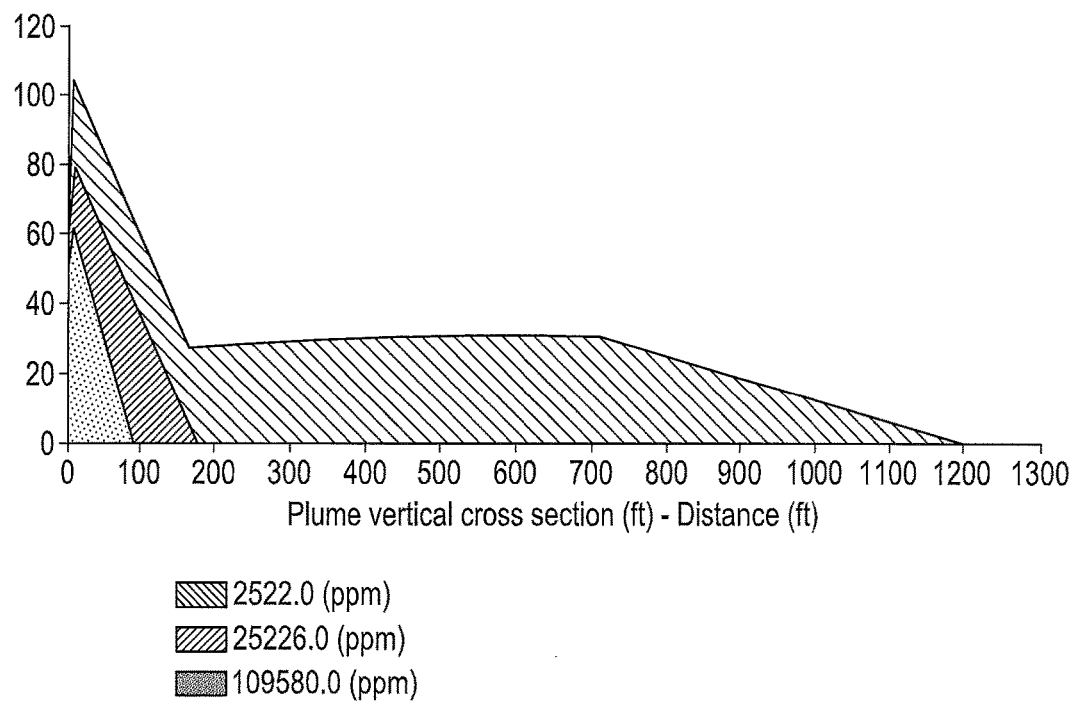
Figure 5:
FIG. 5 illustrates the real composition of volatile organic compounds (VOCs) from passive sampling in hydraulic fracking sites.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

Embodiments are generally directed to the measurement of hydrocarbon gases that are heavier than air in hydraulic fracking sites. Such measurement uses one or more gas detection technologies and analyzes the gas constituent data in real-time in order to trigger safety controls at a fracking site.

More specifically, the use of photo ionization detection (PID), in addition to infra-red (IR), electrochemical, and catalytic bead lower explosive level (LEL) technologies to detect a variety of hydrocarbons and explosive gases from the hydraulic fracking process is disclosed. Also, a method of theoretical prediction of correction factors (instrument gas response relative to target/calibration gas) was developed for individual components that allow custom correction factors for flammable gas mixtures. In addition, a method of placement of gas detectors around a hydraulic fracking site to measure and alert for harmful emissions based on gas diffusion, dispersion and composition (FIG. 2-5) is described. Further, a method to measure a broad range of chemical constituents of gases including flammable, toxic, and hazardous gases is disclosed.

Example 1 Analytical Lab Measurements from Hydraulic Fracking Sites

Analytical lab results for C1 through C6 Hydrocarbon Analysis. The samples were analyzed according to modified EPA Method TO-3 for measurement of C1 through >C6 hydrocarbons using a gas chromatograph equipped with a flame ionization detector (FID). This procedure is described in laboratory SOP VOA-TO3C1C6. This method is not included on the laboratory's National Environmental Laboratory Accreditation Program (NELAP) or American Industrial Hygiene Association Laboratory Accreditation Program (AIHA-LAP) scope of accreditation.

The results for this analysis of "C2 as ethane" are ethane only and contain no other C2 isomers. The result for "C3 as propane" is propane only and does not contain any other C3 isomers. The result for "C4 as n butane" contains a mixture of isobutane and n-butane. The results for "C5 as n-pentane" contain a mixture of n-pentane, and isopentane. The results for "C6 as n-hexane" contain a mixture of n-hexane, isohexane, 3-methylpentane, 2,4dimethylbutane, cyclohexane and methylcyclopentane. The total sample mixture was made up of saturated alkanes and saturated cycloalkanes and contain little or non-detectable amounts of alkenes or cycloalkenes.

The samples were also analyzed for volatile organic compounds in accordance with EPA Method TO-15 from the Compendium of Methods for the Determination of Toxic Organic Compounds in Ambient Air, Second Edition (EPA/625/R-96/010b), January 1999. This procedure is described in laboratory SOP VOATO15. The analytical system was comprised of a gas chromatograph/mass spectrometer (GC/MS) interfaced to a whole-air preconcentrator. This method is not included on the laboratory's AIHA-LAP scope of accreditation. Any analytes flagged with an X are not included on the laboratory's NELAP or DoD-ELAP scope of accreditation. The Summa canisters were cleaned, prior to sampling, down to the method reporting limit (MRL) reported for this project. Projects which require reporting below the MRL could have results between the MRL and method detection limit (MDL) that are biased high. The analytical results are given below:

| Compound | Result ppmV | MRL ppmV | Data Qualifier |
|---|---|---|---|
| Methane | 170,000 | 6.5 | |
| $C_2$ as Ethane | 230,000 | 6.5 | E |
| $C_3$ as Propane | 160,000 | 6.5 | E |
| $C_4$ as n-Butane | 74,000 | 6.5 | E |
| $C_5$ as n-Pentane | 30,000 | 6.5 | |
| $C_6$ as n-Hexane | 14,000 | 6.5 | |
| $C_6$+ as n-Hexane | 20,000 | 13 | |

ND=Compound was analyzed for, but not detected above the laboratory reporting limit.

MRL=Method Reporting Limit—The minimum quantity of a target analyte that can be confidently determined by the referenced method.

E=Estimated; concentration exceeded calibration range.

| Compound | Result ppmV | MRL ppmV | Data Qualifier |
|---|---|---|---|
| Methane | 4,000 | 0.72 | |
| $C_2$ as Ethane | 730 | 0.72 | |
| $C_3$ as Propane | 210 | 0.72 | |
| $C_4$ as n-Butane | 81 | 0.72 | |
| $C_5$ as n-Pentane | 42 | 0.72 | |
| $C_6$ as n-Hexane | 34 | 0.72 | |
| $C_6$+ as n-Hexane | 150 | 1.4 | |

| Compound | Result ppmV | MRL ppmV | Data Qualifier |
|---|---|---|---|
| Methane | 180,000 | 7.0 | |
| $C_2$ as Ethane | 170,000 | 7.0 | E |
| $C_3$ as Propane | 140,000 | 7.0 | E |
| $C_4$ as n-Butane | 81,000 | 7.0 | E |
| $C_5$ as n-Pentane | 35,000 | 7.0 | |
| $C_6$ as n-Hexane | 17,000 | 7.0 | |
| $C_6$+ as n-Hexane | 31,000 | 14 | |

| Compound | Result ppmV | MRL ppmV | Data Qualifier |
|---|---|---|---|
| Methane | 140 | 0.70 | |
| $C_2$ as Ethane | 24 | 0.70 | |
| $C_3$ as Propane | 7.0 | 0.70 | |
| $C_4$ as n-Butane | 2.5 | 0.70 | |
| $C_5$ as n-Pentane | 0.91 | 0.70 | |
| $C_6$ as n-Hexane | ND | 0.70 | |
| $C_6$+ as n-Hexane | 2.3 | 1.4 | |

| Compound | Spike Amount ppmV | Result ppmV | % Recovery | ALS Acceptance Limits | Data Qualifier |
|---|---|---|---|---|---|
| Methane | 1,020 | 1,090 | 107 | 82-108 | |
| Ethane | 1,010 | 1,100 | 109 | 87-113 | |
| Propane | 1,010 | 1,090 | 108 | 85-113 | |
| n-Butane | 1,010 | 1,020 | 101 | 86-113 | |
| n-Pentane | 1,010 | 1,060 | 105 | 80-116 | |
| n-Hexane | 1,020 | 1,030 | 101 | 69-130 | |

| CAS # | Compound | Result µg/m³ | MRL µg/m³ | Result ppbV | MRL ppbV |
|---|---|---|---|---|---|
| 115-07-1 | Propene | ND | 32,000 | ND | 19,000 |
| 75-71-8 | Dichlorodifluoromethane (CFC12) | ND | 32,000 | ND | 6,500 |
| 74-87-3 | Chloromethane | ND | 32,000 | ND | 16,000 |
| 76-14-2 | 1,2-Dichloro-1,1,2,2-tetrafluoroethane (CFC 114) | ND | 32,000 | ND | 4,600 |
| 75-01-4 | Vinyl Chloride | ND | 32,000 | ND | 13,000 |
| 106-99-0 | 1,3-Butadiene | ND | 32,000 | ND | 15,000 |
| 74-83-9 | Bromomethane | ND | 32,000 | ND | 8,300 |
| 75-00-3 | Chloroethane | ND | 32,000 | ND | 12,000 |
| 64-17-5 | Ethanol | ND | 320,000 | ND | 170,000 |
| 75-05-8 | Acetonitrile | ND | 32,000 | ND | 19,000 |
| 107-02-8 | Acrolein | ND | 130,000 | ND | 56,000 |
| 67-64-1 | Acetone | ND | 320,000 | ND | 140,000 |
| 75-69-4 | Trichlorofluoromethane | ND | 32,000 | ND | 5,700 |
| 67-63-0 | 2-Propanol (Isopropyl Alcohol) | ND | 320,000 | ND | 130,000 |
| 107-13-1 | Acrylonitrile | ND | 32,000 | ND | 15,000 |
| 75-35-4 | 1,1-Dichloroethene | ND | 32,000 | ND | 8,100 |
| 75-09-2 | Methylene Chloride | ND | 32,000 | ND | 9,300 |
| 107-05-1 | 3-Chloro-1-propene (Allyl Chloride) | ND | 32,000 | ND | 10,000 |
| 76-13-1 | Trichlorotrifluoroethane | ND | 32,000 | ND | 4,200 |
| 75-15-0 | Carbon Disulfide | ND | 320,000 | ND | 100,000 |

-continued

| CAS # | Compound | Result μg/m³ | MRL μg/m³ | Result ppbV | MRL ppbV |
|---|---|---|---|---|---|
| 156-60-5 | trans-1,2-Dichloroethene | ND | 32,000 | ND | 8,100 |
| 75-34-3 | 1,1-Dichloroethane | ND | 32,000 | ND | 8,000 |
| 1634-04-4 | Methyl tert-Butyl Ether | ND | 32,000 | ND | 8,900 |
| 108-05-4 | Vinyl Acetate | ND | 320,000 | ND | 92,000 |
| 78-93-3 | 2-Butanone (MEK) | ND | 320,000 | ND | 110,000 |

| CAS # | Compound | Result μg/m³ | MRL μg/m³ | Result ppbV | MRL ppbV |
|---|---|---|---|---|---|
| 156-59-2 | cis-1,2-Dichloroethene | ND | 32,000 | ND | 8,100 |
| 141-78-6 | Ethyl Acetate | ND | 65,000 | ND | 18,000 |
| 110-54-3 | n-Hexane | 3,800,000 | 32,000 | 1,100,000 | 9,200 |
| 67-66-3 | Chloroform | ND | 32,000 | ND | 6,600 |
| 109-99-9 | Tetrahydrofuran (THF) | ND | 32,000 | ND | 11,000 |
| 107-06-2 | 1,2-Dichloroethane | ND | 32,000 | ND | 8,000 |
| 71-55-6 | 1,1,1-Trichloroethane | ND | 32,000 | ND | 5,900 |
| 71-43-2 | Benzene | 80,000 | 32,000 | 25,000 | 10,000 |
| 56-23-5 | Carbon Tetrachloride | ND | 32,000 | ND | 5,100 |
| 110-82-7 | Cyclohexane | 500,000 | 65,000 | 150,000 | 19,000 |
| 78-87-5 | 1,2-Dichloropropane | ND | 32,000 | ND | 7,000 |
| 75-27-4 | Bromodichloromethane | ND | 32,000 | ND | 4,800 |
| 79-01-6 | Trichloroethene | ND | 32,000 | ND | 6,000 |
| 123-91-1 | 1,4-Dioxane | ND | 32,000 | ND | 9,000 |
| 80-62-6 | Methyl Methacrylate | ND | 65,000 | ND | 16,000 |
| 142-82-5 | n-Heptane | 1,400,000 | 32,000 | 340,000 | 7,900 |
| 10061-01-5 | cis-1,3-Dichloropropene | ND | 32,000 | ND | 7,100 |
| 108-10-1 | 4-Methyl-2-pentanone | ND | 32,000 | ND | 7,900 |
| 10061-02-6 | trans-1,3-Dichloropropene | ND | 32,000 | ND | 7,100 |
| 79-00-5 | 1,1,2-Trichloroethane | ND | 32,000 | ND | 5,900 |
| 108-88-3 | Toluene | 190,000 | 32,000 | 50,000 | 8,600 |
| 591-78-6 | 2-Hexanone | ND | 32,000 | ND | 7,900 |
| 124-48-1 | Dibromochloromethane | ND | 32,000 | ND | 3,800 |
| 106-93-4 | 1,2-Dibromoethane | ND | 32,000 | ND | 4,200 |
| 123-86-4 | n-Butyl Acetate | ND | 32,000 | ND | 6,800 |

| CAS # | Compound | Result μg/m³ | MRL μg/m³ | Result ppbV | MRL ppbV |
|---|---|---|---|---|---|
| 115-07-1 | Propene | ND | 1.4 | ND | 0.81 |
| 75-71-8 | Dichlorodifluoromethane (CFC12) | 1.9 | 1.4 | 0.38 | 0.28 |
| 74-87-3 | Chloromethane | ND | 1.4 | ND | 0.68 |
| 76-14-2 | 1,2-Dichloro-1,1,2,2-tetrafluoroethane (CFC 114) | ND | 1.4 | ND | 0.20 |
| 75-01-4 | Vinyl Chloride | ND | 1.4 | ND | 0.55 |
| 106-99-0 | 1,3-Butadiene | ND | 1.4 | ND | 0.63 |
| 74-83-9 | Bromomethane | ND | 1.4 | ND | 0.36 |
| 75-00-3 | Chloroethane | ND | 1.4 | ND | 0.53 |
| 64-17-5 | Ethanol | ND | 14 | ND | 7.4 |
| 75-05-8 | Acetonitrile | ND | 1.4 | ND | 0.83 |
| 107-02-8 | Acrolein | ND | 5.6 | ND | 2.4 |
| 67-64-1 | Acetone | ND | 14 | ND | 5.9 |
| 75-69-4 | Trichlorofluoromethane | ND | 1.4 | ND | 0.25 |
| 67-63-0 | 2-Propanol (Isopropyl Alcohol) | ND | 14 | ND | 5.7 |
| 107-13-1 | Acrylonitrile | ND | 1.4 | ND | 0.65 |
| 75-35-4 | 1,1-Dichloroethene | ND | 1.4 | ND | 0.35 |
| 75-09-2 | Methylene Chloride | ND | 1.4 | ND | 0.40 |
| 107-05-1 | 3-Chloro-1-propene (Allyl Chloride) | ND | 1.4 | ND | 0.45 |
| 76-13-1 | Trichlorotrifluoroethane | ND | 1.4 | ND | 0.18 |
| 75-15-0 | Carbon Disulfide | ND | 14 | ND | 4.5 |
| 156-60-5 | trans-1,2-Dichloroethene | ND | 1.4 | ND | 0.35 |
| 75-34-3 | 1,1-Dichloroethane | ND | 1.4 | ND | 0.35 |
| 1634-04-4 | Methyl tert-Butyl Ether | ND | 1.4 | ND | 0.39 |
| 108-05-4 | Vinyl Acetate | ND | 14 | ND | 4.0 |
| 78-93-3 | 2-Butanone (MEK) | ND | 14 | ND | 4.7 |

| CAS # | Compound | Result µg/m³ | MRL µg/m³ | Result ppbV | MRL ppbV |
|---|---|---|---|---|---|
| 156-59-2 | cis-1,2-Dichloroethene | ND | 1.4 | ND | 0.35 |
| 141-78-6 | Ethyl Acetate | 4.6 | 2.8 | 1.3 | 0.78 |
| 110-54-3 | n-Hexane | 330 | 14 | 95 | 4.0 |
| 67-66-3 | Chloroform | ND | 1.4 | ND | 0.29 |
| 109-99-9 | Tetrahydrofuran (THF) | ND | 1.4 | ND | 0.47 |
| 107-06-2 | 1,2-Dichloroethane | ND | 1.4 | ND | 0.35 |
| 71-55-6 | 1,1,1-Trichloroethane | ND | 1.4 | ND | 0.26 |
| 71-43-2 | Benzene | 11 | 1.4 | 3.4 | 0.44 |
| 56-23-5 | Carbon Tetrachloride | ND | 1.4 | ND | 0.22 |
| 110-82-7 | Cyclohexane | 52 | 2.8 | 15 | 0.81 |
| 78-87-5 | 1,2-Dichloropropane | ND | 1.4 | ND | 0.30 |
| 75-27-4 | Bromodichloromethane | ND | 1.4 | ND | 0.21 |
| 79-01-6 | Trichloroethene | ND | 1.4 | ND | 0.26 |
| 123-91-1 | 1,4-Dioxane | ND | 1.4 | ND | 0.39 |
| 80-62-6 | Methyl Methacrylate | ND | 2.8 | ND | 0.68 |
| 142-82-5 | n-Heptane | 140 | 1.4 | 34 | 0.34 |
| 10061-01-5 | cis-1,3-Dichloropropene | ND | 1.4 | ND | 0.31 |
| 108-10-1 | 4-Methyl-2-pentanone | ND | 1.4 | ND | 0.34 |
| 10061-02-6 | trans-1,3-Dichloropropene | ND | 1.4 | ND | 0.31 |
| 79-00-5 | 1,1,2-Trichloroethane | ND | 1.4 | ND | 0.26 |
| 108-88-3 | Toluene | 21 | 1.4 | 5.5 | 0.37 |
| 591-78-6 | 2-Hexanone | ND | 1.4 | ND | 0.34 |
| 124-48-1 | Dibromochloromethane | ND | 1.4 | ND | 0.16 |
| 106-93-4 | 1,2-Dibromoethane | ND | 1.4 | ND | 0.18 |
| 123-86-4 | n-Butyl Acetate | ND | 1.4 | ND | 0.29 |

| CAS # | Compound | Result µg/m³ | MRL µg/m³ | Result ppbV | MRL ppbV |
|---|---|---|---|---|---|
| 156-59-2 | cis-1,2-Dichloroethene | ND | 23,000 | ND | 5,900 |
| 141-78-6 | Ethyl Acetate | ND | 47,000 | ND | 13,000 |
| 110-54-3 | n-Hexane | 5,900,000 | 70,000 | 1,700,000 | 20,000 |
| 67-66-3 | Chloroform | ND | 23,000 | ND | 4,800 |
| 109-99-9 | Tetrahydrofuran (THF) | ND | 23,000 | ND | 7,900 |
| 107-06-2 | 1,2-Dichloroethane | ND | 23,000 | ND | 5,800 |
| 71-55-6 | 1,1,1-Trichloroethane | ND | 23,000 | ND | 4,300 |
| 71-43-2 | Benzene | 210,000 | 23,000 | 66,000 | 7,300 |
| 56-23-5 | Carbon Tetrachloride | ND | 23,000 | ND | 3,700 |
| 110-82-7 | Cyclohexane | 1,400,000 | 47,000 | 410,000 | 14,000 |
| 78-87-5 | 1,2-Dichloropropane | ND | 23,000 | ND | 5,100 |
| 75-27-4 | Bromodichloromethane | ND | 23,000 | ND | 3,500 |
| 79-01-6 | Trichloroethene | ND | 23,000 | ND | 4,300 |
| 123-91-1 | 1,4-Dioxane | ND | 23,000 | ND | 6,500 |
| 80-62-6 | Methyl Methacrylate | ND | 47,000 | ND | 11,000 |
| 142-82-5 | n-Heptane | 4,000,000 | 23,000 | 990,000 | 5,700 |
| 10061-01-5 | cis-1,3-Dichloropropene | ND | 23,000 | ND | 5,100 |
| 108-10-1 | 4-Methyl-2-pentanone | ND | 23,000 | ND | 5,700 |
| 10061-02-6 | trans-1,3-Dichloropropene | ND | 23,000 | ND | 5,100 |
| 79-00-5 | 1,1,2-Trichloroethane | ND | 23,000 | ND | 4,300 |
| 108-88-3 | Toluene | 520,000 | 23,000 | 140,000 | 6,200 |
| 591-78-6 | 2-Hexanone | ND | 23,000 | ND | 5,700 |
| 124-48-1 | Dibromochloromethane | ND | 23,000 | ND | 2,700 |
| 106-93-4 | 1,2-Dibromoethane | ND | 23,000 | ND | 3,000 |
| 123-86-4 | n-Butyl Acetate | ND | 23,000 | ND | 4,900 |

| CAS # | Compound | Result µg/m³ | MRL µg/m³ | Result ppbV | MRL ppbV |
|---|---|---|---|---|---|
| 111-65-9 | n-Octane | 1,200,000 | 23,000 | 250,000 | 5,000 |
| 127-18-4 | Tetrachloroethene | ND | 23,000 | ND | 3,400 |
| 108-90-7 | Chlorobenzene | ND | 23,000 | ND | 5,100 |
| 100-41-4 | Ethylbenzene | 27,000 | 23,000 | 6,100 | 5,400 |
| 179601-23-1 | m,p-Xylenes | 240,000 | 47,000 | 55,000 | 11,000 |
| 75-25-2 | Bromoform | ND | 23,000 | ND | 2,300 |
| 100-42-5 | Styrene | ND | 23,000 | ND | 5,500 |
| 95-47-6 | o-Xylene | 35,000 | 23,000 | 8,100 | 5,400 |
| 111-84-2 | n-Nonane | 280,000 | 23,000 | 53,000 | 4,400 |
| 79-34-5 | 1,1,2,2-Tetrachloroethane | ND | 23,000 | ND | 3,400 |
| 98-82-8 | Cumene | ND | 23,000 | ND | 4,700 |
| 80-56-8 | alpha-Pinene | ND | 23,000 | ND | 4,200 |
| 103-65-1 | n-Propylbenzene | ND | 23,000 | ND | 4,700 |

-continued

| CAS # | Compound | Result μg/m³ | MRL μg/m³ | Result ppbV | MRL ppbV |
|---|---|---|---|---|---|
| 622-96-8 | 4-Ethyltoluene | ND | 23,000 | ND | 4,700 |
| 108-67-8 | 1,3,5-Trimethylbenzene | ND | 23,000 | ND | 4,700 |
| 95-63-6 | 1,2,4-Trimethylbenzene | ND | 23,000 | ND | 4,700 |
| 100-44-7 | Benzyl Chloride | ND | 23,000 | ND | 4,500 |
| 541-73-1 | 1,3-Dichlorobenzene | ND | 23,000 | ND | 3,900 |
| 106-46-7 | 1,4-Dichlorobenzene | ND | 23,000 | ND | 3,900 |
| 95-50-1 | 1,2-Dichlorobenzene | ND | 23,000 | ND | 3,900 |
| 5989-27-5 | d-Limonene | ND | 23,000 | ND | 4,200 |
| 96-12-8 | 1,2-Dibromo-3-chloropropane | ND | 23,000 | ND | 2,400 |
| 120-82-1 | 1,2,4-Trichlorobenzene | ND | 23,000 | ND | 3,100 |
| 91-20-3 | Naphthalene | ND | 23,000 | ND | 4,500 |
| 87-68-3 | Hexachlorobutadiene | ND | 23,000 | ND | 2,200 |

Correction Factor Development:

Correction factors (CFs) relate to the sensitivity of the target gas detection relative to the calibration gas detection, under identical conditions. CFs are mathematical scaling factors that enable the user to quantify a larger number of gaseous chemicals using only a single calibration gas. For gas sensors that use catalytic bead technology, methane is the most widely used calibration gas. CFs can be obtained by comparison of the target gas response relative to the methane response or can be predicted based on diffusion theory. A well-known diffusion theory is based on Graham's Law. See wikipedia.org/wiki/Graham's_law. According to Graham's law, the gas velocity is inversely proportional to the square root of the mass of its molecules:

$$\frac{V_1}{V_2} = \frac{\sqrt{MW_2}}{\sqrt{MW_1}}$$

where V1 and V2 are the gases' velocity and MW1 and MW2 are the respective molecular weights of the gases.

Although this theory has been used in connection with known techniques, it has been unable to give predictably reliable CFs when gases with different functional substituents are measured. This theory doesn't take into account dispersion interaction in between the gas molecules due to their different polarity. Dispersion interaction of the gas molecules could create conglomerated clouds rather than even molecular distribution in the volume that slows down gas diffusion.

Figure 6:
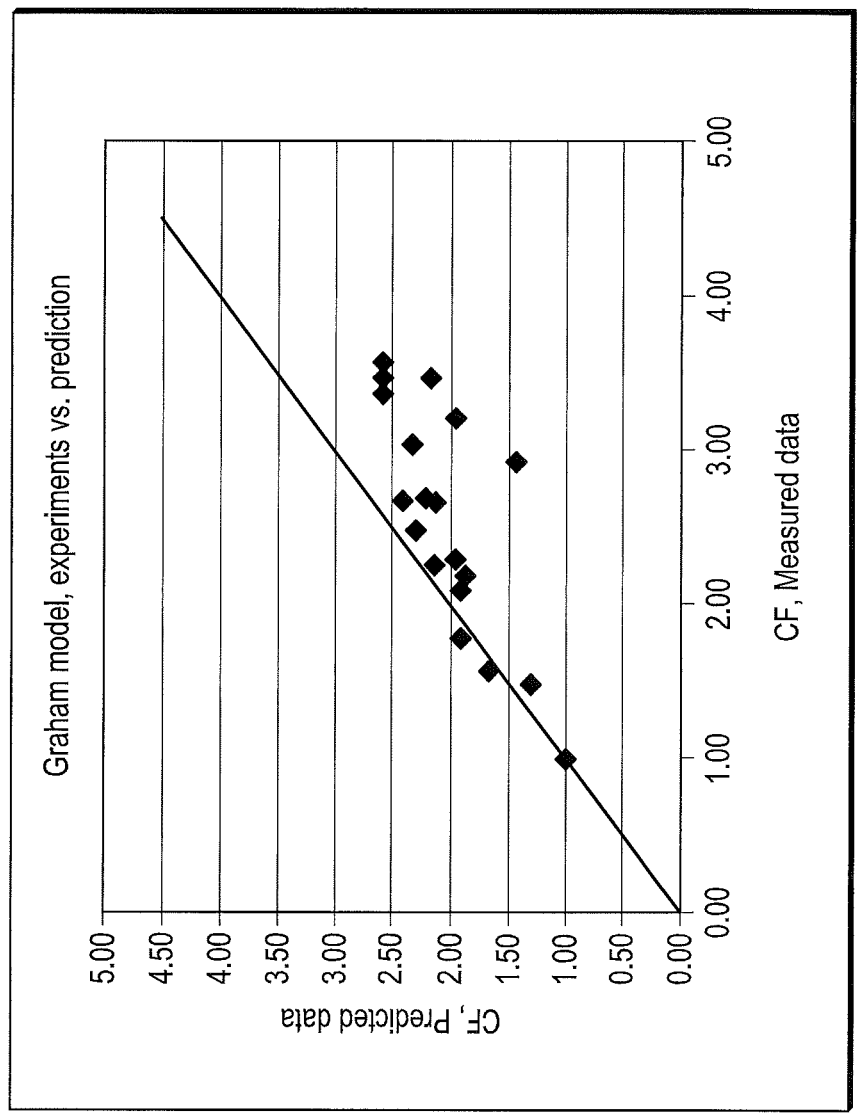
FIG. 6 illustrates experimental CF measurements and comparison data with predicted data.

Experimental CF measurements and comparison data with predicted data is shown in FIG. 6. As shown in FIG. 6, the blue line is the ideal case when the theory follows the practical data.

One embodiment of the present invention teaches a modification of the Graham equation by taking molecular interactions into account. Here, the measure of the gas molecules' interactions is the boiling temperature (BP) of their liquid state. At the boiling point, the liquid state is transformed to a gas state. To do such a transformation, sufficient energy needs to be applied to break apart the molecules' associations in the liquid. The value of energy depends on the dispersion forces that keep the molecules associated with each other. This means dispersion forces are proportional to the boiling points of liquids normalized to their molecular weight.

The following equation outlines embodiments of the correction factor that include both diffusion and dispersion coefficients in the calculation of the correction factor.

$$CF_{CH4}^{gas} = \frac{\sqrt{MW_{gas} + \frac{BP^x}{K \times MW_{gas}^y}}}{\sqrt{MW_{CH4}}}$$

Figure 7:
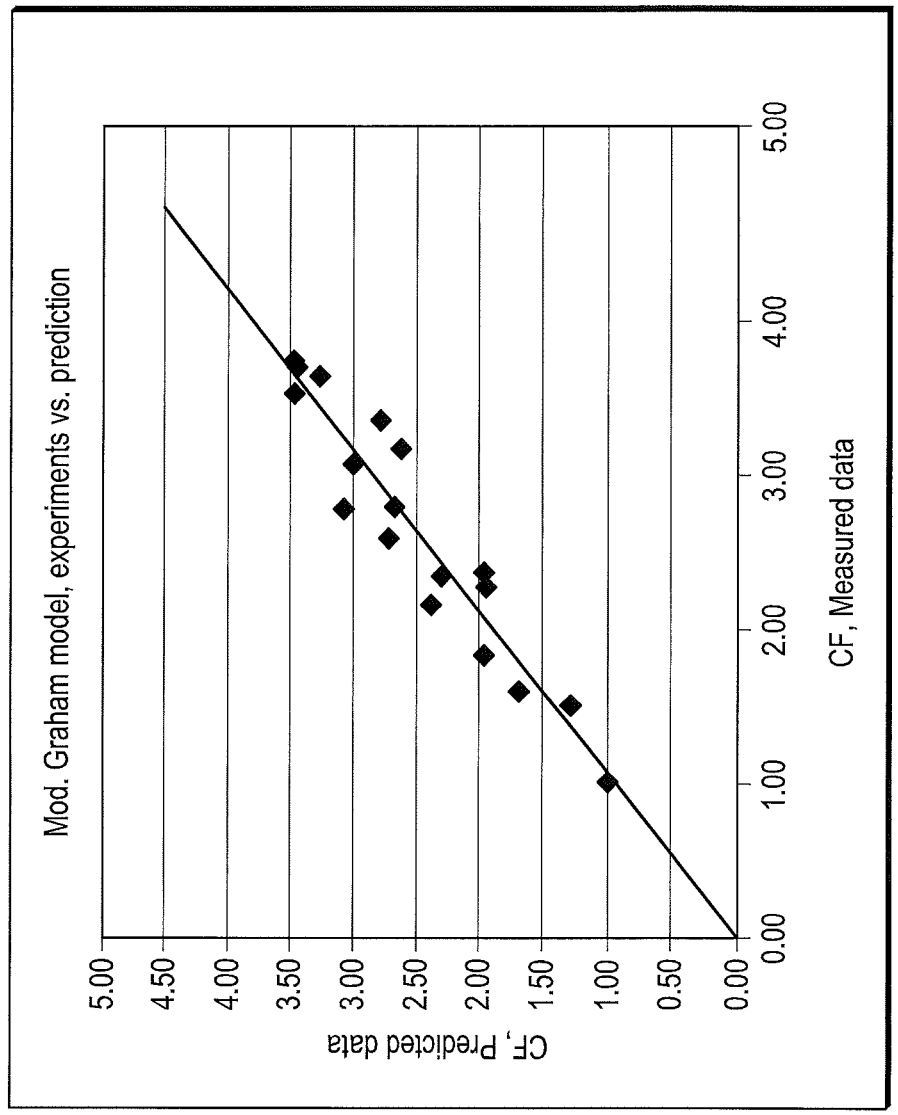
FIG. 7 illustrates the new modified Graham model, which shows better predictability for correction factors.
Figure 8:
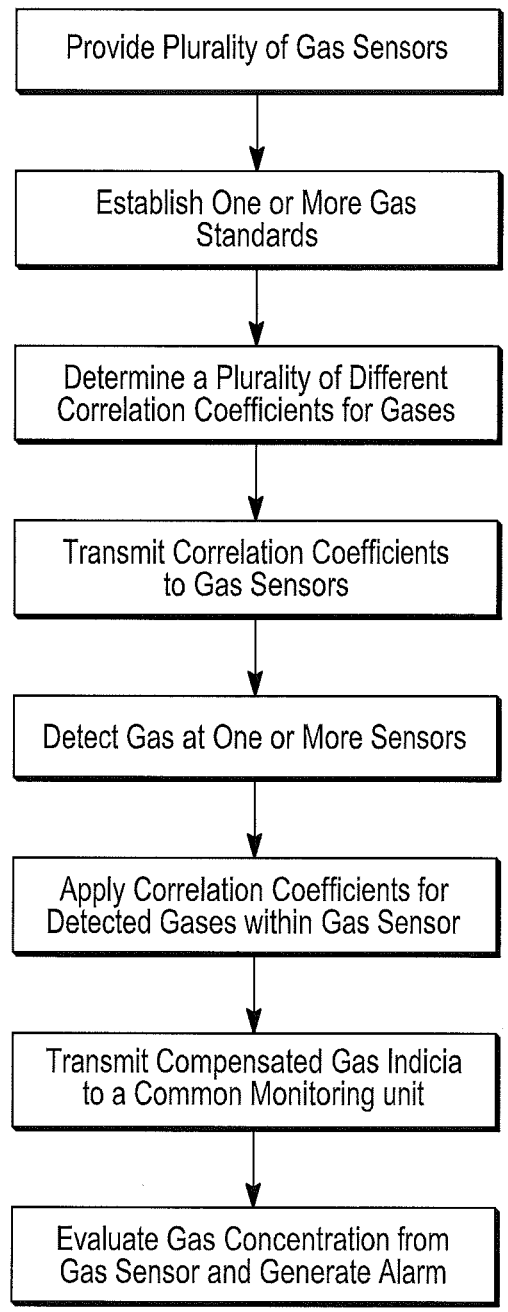
FIG. 8 illustrates a method of monitoring gases at a hydraulic fracking site.
Figure 9:
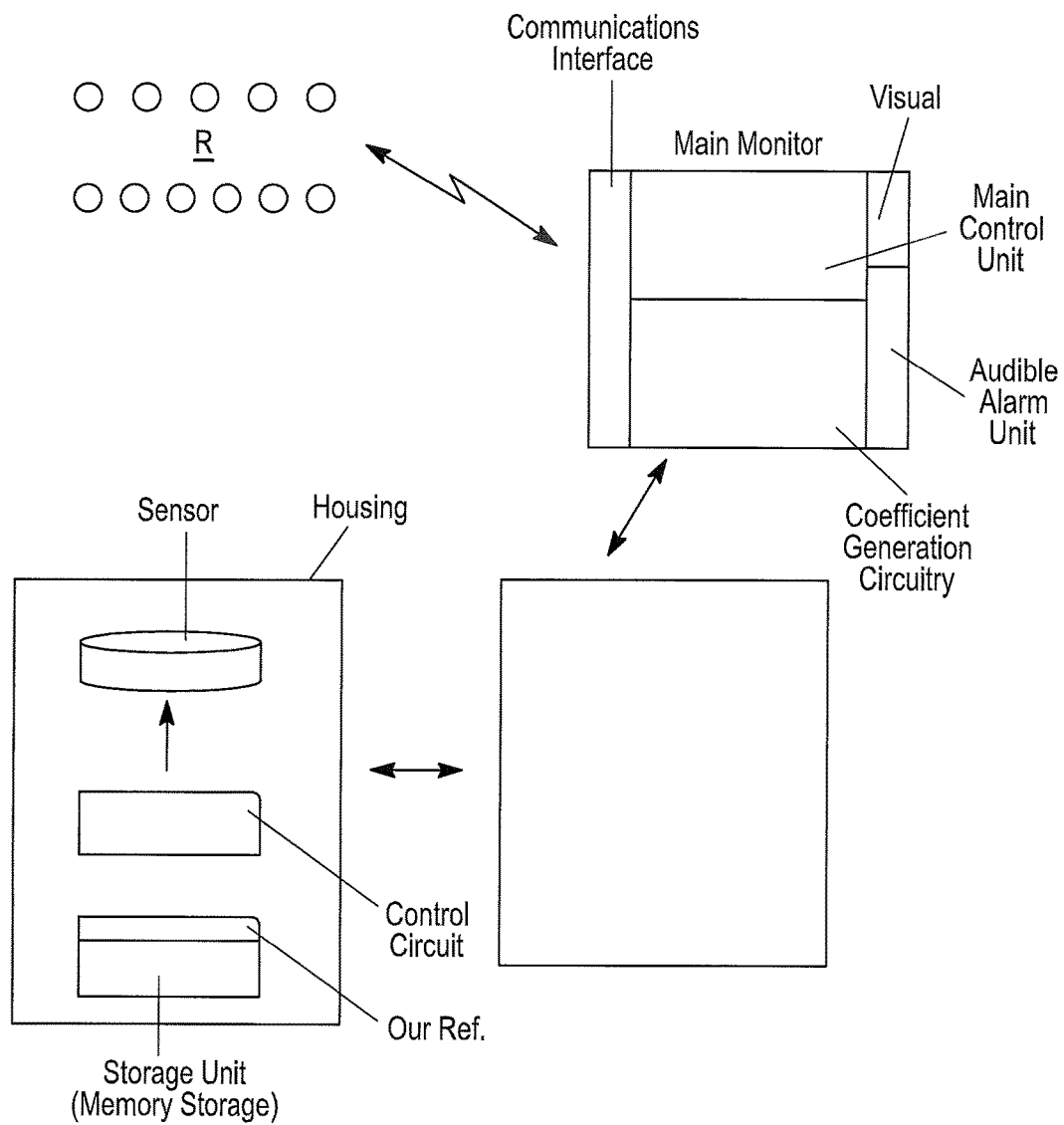
FIG. 9 illustrates a gas detection system for monitoring a hydraulic fracking site.

The values of K, x, and y depend on the specific catalytic bead sensor's design and are found by the fitting where x and y can be any number greater than or equal to zero (0), and where K is greater than zero (0). According to embodiments disclosed herein, this alternative Graham-type equation is better able to accurately predict a correction factor for individual components (see FIG. 7).

This method of determining an accurate response to a LEL gas detector includes developing a custom system correction factor, said factor taking into account a molecular diffusive part and intermolecular interaction part; providing an LEL sensing element which incorporates Graham's diffusion law to determine the diffusive part, the dispersive part being calculated based on a boiling point relative to the molecular weight of the gases; and using a system correction by applying heavier hydrocarbon measurements in a hydraulic site to ensure the safety of the site, workers and to improve productivity.

In one embodiment, an apparatus for gas measurement at a hydraulic fracking site includes a gas sensor having a detection technology selected from the group consisting of a photo ionization detection, lower explosion level detection, infra-red detection, and electrochemical detection; and a computer in communication with the gas sensor wherein the computer generates a correction factor and applies the correction factor to a detected gas signal.

The apparatus can also contain an alarm that operates when the corrected gas signal meets a predetermined level. Placement of gas sensor at the fracking site is guided by meteorological parameters including temperature, wind direction, and humidity at the hydraulic fracking site.

As discussed above, the correction factor includes both diffusion and dispersion coefficients of the gas and has the formula:

$$CF_{CH4}^{gas} = \frac{\sqrt{MW_{gas} + \frac{BP^x}{K \times MW_{gas}^y}}}{\sqrt{MW_{CH4}}}$$

wherein MW refers to molecular weight of the gas, BP refers to the boiling point of the gas, x and y can be any number greater than or equal to zero (0), and K is greater than zero (0).

In another embodiment, a method of gas measurement at a hydraulic fracking site includes calibrating a gas sensor present at the site with methane gas so that the sensor output reflects methane percent equivalents; operating the gas sensor to record a gas constituent present at the site; generating gas constituent data in methane percent equivalents; multiplying a calculated correlation factor and the gas constituent's methane percent equivalents to obtain a corrected gas constituent level; and triggering safety controls in the hydraulic fracking site if the corrected gas constituent level is found to be over a predetermined limit.

The method uses the correction factor described above having the formula:

$$CF_{CH4}^{gas} = \frac{\sqrt{MW_{gas} + \frac{BP^x}{K \times MW_{gas}^y}}}{\sqrt{MW_{CH4}}}$$

wherein MW refers to molecular weight of the gas, BP refers to the boiling point of the gas, x and y can be any number greater than or equal to zero (0), and K is greater than zero (0).

Yet another contemplated method of monitoring emissions at a fracking site includes providing a gas sensor at a hydraulic fracking site; calibrating the gas sensor to one or more gas standards; determining a correlation coefficients for a gas; transmitting the correlation coefficient for the gas to the gas sensor; measuring the gas at the sensor to provide an indicia of an amount of detected gas present at the fracking site; applying the correlation coefficient to the indicia of detected gas; transmitting the corrected indicia of detected gas to a monitoring unit; comparing the corrected indicia of detected gas with a predetermined level for alarm; and generating an alarm if the predetermined level for alarm is met. The gas standard can be methane or any other suitable gas.

In still another embodiment, a contemplated system encompasses a first housing comprising a gas sensor, a control circuit in communication with the gas sensor, and a memory storage unit in communication with the control circuit; and a second housing comprising a main monitor including a communications interface in communication with the control circuit, correlation coefficient circuitry in communication with the communications interface, and an alarm unit in communication with the communications interface.

Here, as above, the gas sensor comprises a detection technology selected from the group consisting of a photo ionization detection, lower explosion level detection, infrared detection, and electrochemical detection. The correlation coefficients circuitry calculates a corrected signal for a gas based on a formula for a correction factor of:

$$CF_{CH4}^{gas} = \frac{\sqrt{MW_{gas} + \frac{BP^x}{K \times MW_{gas}^y}}}{\sqrt{MW_{CH4}}}$$

wherein MW refers to molecular weight of the gas, BP refers to the boiling point of the gas, x and y can be any number greater than or equal to zero (0), and K is greater than zero (0).

The gas sensor can be calibrated with a gas selected from the group consisting of methane gas, propane gas, and pentane gas. In some cases, the gas sensor is calibrated with methane gas. The correction factor is multiplied by a gas sensor reading before or after calibration with methane gas. The system can include multiple housings and gas sensors. The alarm unit can comprises an audible alarm and a visual alarm or just one alarm. In one instance, the correction factor is preloaded in the memory storage unit. In another instance, the correction factor is calculated in real-time at the site. The housings can be explosion-proof.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

What is claimed is:

1. A method of gas measurement at a hydraulic fracking site using a gas measurement system comprising a gas sensor disposed within a first housing and present at the hydraulic fracking site and a computer in signal communication with the gas sensor and including a control circuit and a memory storage unit in communication with the control circuit, wherein the gas sensor comprises a photo ionization detector, a lower explosion level detector, an infra-red detector, or an electrochemical detector, the method comprising:
   (a) calibrating the gas sensor with methane gas so that the sensor output reflects methane percent equivalents;
   (b) operating the gas sensor to record a gas constituent present at the hydraulic fracking site;
   (c) generating, by the gas sensor, gas constituent data in methane percent equivalents;
   (d) multiplying, by the computer, a calculated correlation factor and the gas constituent's methane percent equivalents to obtain a corrected gas constituent level, wherein the calculated correlation factor has a value of:

$$CF_{CH4}^{gas} = \frac{\sqrt{MW_{gas} + \frac{BP^x}{K \times MW_{gas}^y}}}{\sqrt{MW_{CH4}}}$$

wherein MW refers to molecular weight of the gas, BP refers to the boiling point of the gas, x and y are any number greater than or equal to zero (0), and K is greater than zero (0);
   (e) determining, by the computer, that the corrected gas constituent level is over a predetermined limit; and
   (f) triggering safety controls in the hydraulic fracking site based on step (e).

2. The method of claim 1, wherein the factor takes into account a molecular diffusive part and intermolecular interaction part of the gas constituent.

3. A method of monitoring emissions at a fracking site using a gas measurement system comprising a gas sensor present at the hydraulic fracking site in a first housing, a computer in signal communication with the gas sensor and including a control circuit and a memory storage unit in communication with the control circuit, wherein the gas sensor comprises a photo ionization detector, a lower explosion level detector, an infra-red detector, or an electrochemical detector, the method comprising:
(a) providing the gas sensor;
(b) calibrating the gas sensor to one or more gas standards;
(c) determining, by the computer, a correlation coefficient for a gas, wherein the correlation coefficient has a value of:

$$CF_{CH4}^{gas} = \frac{\sqrt{MW_{gas} + \frac{BP^x}{K \times MW_{gas}^y}}}{\sqrt{MW_{CH4}}}$$

wherein MW refers to molecular weight of the gas, BP refers to the boiling point of the gas, x and y are any number greater than or equal to zero (0), and K is greater than zero (0);
(d) transmitting the correlation coefficient for the gas to the gas sensor;
(e) measuring, by the gas sensor, the gas to provide indicia of an amount of detected gas present at the fracking site;
(f) applying the correlation coefficient to the indicia of detected gas;
(g) transmitting the corrected indicia of detected gas to a monitoring unit;
(h) comparing, by the monitoring unit, the corrected indicia of detected gas with a predetermined level for alarm; and
(i) generating an alarm if the predetermined level for alarm is met.

4. The method of claim 3 wherein the gas standard is methane.

5. A system for gas measurement at a hydraulic fracking site, the system comprising:
(a) a first housing present at the hydraulic fracking site and comprising a gas sensor configured to record a gas reading present at the hydraulic fracking site, a control circuit in communication with the gas sensor, and a memory storage unit in communication with the control circuit, wherein the gas sensor comprises a photo ionization detector, a lower explosion level detector, an infra-red detector, or an electrochemical detector;
(b) a second housing comprising a main monitor including a communications interface in communication with the control circuit, correlation coefficient circuitry in communication with the communications interface, and an alarm unit in communication with the communications interface,
wherein the correlation coefficient circuitry calculates a corrected gas constituent level based on a value for a correction factor of:

$$CF_{CH4}^{gas} = \frac{\sqrt{MW_{gas} + \frac{BP^x}{K \times MW_{gas}^y}}}{\sqrt{MW_{CH4}}}$$

wherein MW refers to molecular weight of the gas, BP refers to the boiling point of the gas, x and y are any number greater than or equal to zero (0), and K is greater than zero (0), and
wherein the alarm unit is configured to generate an alarm if the control circuit determines that the corrected gas constituent level is over a predetermined limit.

6. The system of claim 5 wherein the gas sensor is calibrated with a gas selected from the group consisting of methane gas, propane gas, and pentane gas.

7. The system of claim 5 wherein the correction factor is multiplied by the gas sensor reading before or after calibration with methane gas.

8. The system of claim 5 comprising multiple first housings comprising multiple gas sensors.

9. The system of claim 5 where the alarm unit comprises an audible alarm or a visual alarm or both.

10. The system of claim 5 wherein the correction factor is preloaded in the memory storage unit or is calculated in real-time.

11. The system of claim 5 wherein the gas sensor is calibrated with methane gas.

12. The system of claim 5 wherein the housings are explosion-proof.

13. The method of claim 1, further comprising operating an alarm when the when the safety controls are triggered.

14. The method of claim 1, further comprising placing the gas sensor at the hydraulic fracking site guided by meteorological parameters including temperature, wind direction, and humidity.

15. The method of claim 1, wherein generating the calculated correction factor includes using both diffusion and dispersion coefficients of the gas.

16. The method of claim 1, wherein steps (c)-(e) are performed in real time.

17. The method of claim 1, wherein the gas constituent is one of a combination of flammable, toxic, and hazardous gases at the hydraulic fracking site.

* * * * *